United States Patent
Scheunemann et al.

(10) Patent No.: US 11,304,890 B2
(45) Date of Patent: Apr. 19, 2022

(54) CONDITIONING HAIR TREATMENT PRODUCT WITH WASHOUT PROTECTION

(71) Applicant: Henkel AG & Co. KGaA, Duesseldorf (DE)

(72) Inventors: Volker Scheunemann, Lueneburg (DE); Erik Schulze Zur Wiesche, Hamburg (DE); Rene Krohn, Norderstedt (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 67 days.

(21) Appl. No.: 16/337,289

(22) PCT Filed: Jul. 13, 2017

(86) PCT No.: PCT/EP2017/067690
§ 371 (c)(1),
(2) Date: Mar. 27, 2019

(87) PCT Pub. No.: WO2018/059766
PCT Pub. Date: Apr. 5, 2018

(65) Prior Publication Data
US 2019/0216713 A1  Jul. 18, 2019

(30) Foreign Application Priority Data
Sep. 30, 2016  (DE) ..................... 10 2016 218 984.0

(51) Int. Cl.
| | |
|---|---|
| A61Q 5/02 | (2006.01) |
| A61Q 5/12 | (2006.01) |
| A61K 8/898 | (2006.01) |
| A61K 8/33 | (2006.01) |
| A61K 8/34 | (2006.01) |
| A61K 8/41 | (2006.01) |
| A61K 8/44 | (2006.01) |
| A61K 8/49 | (2006.01) |
| A61K 8/73 | (2006.01) |
| A61Q 5/00 | (2006.01) |

(52) U.S. Cl.
CPC ................ *A61K 8/898* (2013.01); *A61K 8/33* (2013.01); *A61K 8/345* (2013.01); *A61K 8/416* (2013.01); *A61K 8/44* (2013.01); *A61K 8/4913* (2013.01); *A61K 8/731* (2013.01); *A61K 8/737* (2013.01); *A61Q 5/004* (2013.01); *A61Q 5/02* (2013.01); *A61Q 5/12* (2013.01); *A61K 2800/5426* (2013.01); *A61K 2800/592* (2013.01); *A61K 2800/594* (2013.01)

(58) Field of Classification Search
None
See application file for complete search history.

(56) References Cited

U.S. PATENT DOCUMENTS

| | | | |
|---|---|---|---|
| 3,665,072 A | 5/1972 | L'Oreal | |
| 2002/0193264 A1 | 12/2002 | Cannell | |
| 2007/0060489 A1* | 3/2007 | Sun | A61K 8/416 510/119 |
| 2009/0176676 A1* | 7/2009 | Hilvert | A61K 8/0241 510/122 |
| 2013/0319449 A1* | 12/2013 | Xavier | A61Q 5/002 132/209 |
| 2014/0116458 A1* | 5/2014 | Krueger | A61Q 5/004 132/202 |
| 2015/0174052 A1* | 6/2015 | Mette | A61K 8/673 424/70.122 |
| 2019/0091119 A1* | 3/2019 | Dixon | A61K 8/34 |

FOREIGN PATENT DOCUMENTS

| | | |
|---|---|---|
| DE | 102011086633 A1 | 5/2013 |
| DE | 102015223826 A1 | 9/2016 |
| EP | 1938795 A2 | 7/2008 |

OTHER PUBLICATIONS

EPO, International Search Report issued in International Application No. PCT/EP2017/067690, dated Aug. 28, 2017.

* cited by examiner

*Primary Examiner* — Jyothsna A Venkat
(74) *Attorney, Agent, or Firm* — Lorenz & Kopf, LLP

(57) ABSTRACT

Hair treatment products comprising, in relation to its weight, from about 0.001 to about 20% by weight of at least one alpha-substituted aldehyde and from about 0.001 to about 50% by weight of at least one amino-functional silicon, which lead to improved structural reinforcement of keratin fibers and improved hair care, and which reduce or prevent color washout in dyed hair.

9 Claims, No Drawings

CONDITIONING HAIR TREATMENT PRODUCT WITH WASHOUT PROTECTION

CROSS-REFERENCE TO RELATED APPLICATION

This application is a U.S. National-Stage entry under 35 U.S.C. § 371 based on International Application No. PCT/EP2017/067690, filed Jul. 13, 2017, which was published under PCT Article 21(2) and which claims priority to German Application No. 10 2016 218 984.0, filed Sep. 30, 2016, which are all hereby incorporated in their entirety by reference.

TECHNICAL FIELD

The present disclosure relates to hair treatment agents, in particular shampoos and what are referred to as conditioners, having an active ingredient combination for the gentle and effective care of hair.

BACKGROUND

The importance of care products with the longest-lasting possible effect is increasing not least due to the high amount of strain on hair caused, for example, by coloring or permanents, by cleaning hair with shampoos, and by environmental pressures. Care products of this type influence the natural structure and properties of hair. For example, the wet and dry combability, the hold and the volume of hair can be optimized following care treatments of this kind, or hair can be protected from increased splitting.

It has long been customary, therefore, to subject hair to a special aftertreatment. In this process, the hair is treated with special active ingredients, for example quaternary ammonium salts or special polymers, usually in the form of a rinse. As a result of this treatment, depending on the formulation, the combability, the hold, and the volume of the hair are improved, and the amount of splitting is reduced.

Multi-functional cosmetic products are also known in the prior art. These include in particular what are referred to as "2 in 1" shampoos, which not only clean hair but also condition it. Products of this type are held in high esteem by consumers because, due to their product performance, they eradicate the need for at least one process step, for example conditioning with a conventional hair conditioner.

Similarly, products for modifying natural hair color play a prominent role in hair cosmetics. A distinction is made between permanent, semi-permanent, or temporary coloring systems based on chemical and/or natural dyes. Hair colors produced artificially by permanent, semi-permanent or temporary coloring systems are however disadvantageous in that they can change undesirably, for example during or after hair cleaning.

An "undesirable change" is understood to mean fading or bleeding and loss of the color brilliance of the hair shade achieved by the particular coloring. Environmental impacts and/or the effects of sunlight can further intensify these changes.

There continues to be a need to provide active ingredients or active ingredient combinations for hair treatment agents which have good nourishing properties and also strengthen the adhesion of dyes to hair fibers and thus maintain the fastness of the artificially produced hair color, and in this respect to develop hair treatment agents.

It has been observed, however, that water hardness can sometimes negatively influence the nourishing properties of hair treatment agents, and therefore the nourishing performance of the same product may be either too low or too high depending on water quality.

Nourishing performance that is too high or "over-nourishment" (occurrence of what is known as a build-up effect) of the hair is understood to mean in particular a greasy hair feel, lack of hair volume, and/or a lank, unkempt appearance of the hair, whereas damaged hair (broken and dull hair that is prone to splitting) is an indicator of too little nourishing performance.

BRIEF SUMMARY

This disclosure provides a hair treatment agent including, based on its weight,
  a) from about 0.001 to about 20 wt. % of at least one alpha-substituted aldehyde,
  b) from about 0.001 to about 50 wt. % of at least one amino-functional silicone.

This disclosure also provides a method for treating hair, wherein the aforementioned agent is applied to dry or wet hair, is left there for a period of from about 10 to about 300 seconds, and is rinsed out thereafter. This disclosure further provides a method for treating hair wherein the aforementioned agent is applied to dry or wet hair and is left there until the next time the hair is washed.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present application was therefore to provide skin-compatible, nourishing hair treatment agents which have excellent foaming properties, can be rinsed out well with water and additionally reduce or prevent washout of color from colored hair.

The nourishing hair treatment agents should have a uniform conditioning performance irrespective of water quality and in particular should not weigh down fine hair and/or damaged hair, but should strengthen the structure of the hair and thus protect it from splitting and breaking and should improve combability and the feel of the hair. In addition, said agents should have a germicidal effect.

It has now been found that a combination of certain ingredients has a particularly positive effect on colored hair and the hair follicles treated with said ingredients.

A first subject of the present disclosure is hair treatment agents containing, based on their weight,
  a) from about 0.001 to about 20 wt. % of at least one alpha-substituted aldehyde,
  b) from about 0.001 to about 50 wt. % of at least one amino-functional silicone.

Hair treatment agents within the meaning of the present disclosure are, for example, hair shampoos, hair conditioners, conditioning shampoos, hair sprays, hair rinses, hair masks, hair packs, hair tonics, permanent wave fixing solutions, hair coloring shampoos, hair dyes, hair setting lotions, hair setting products, hair styling preparations, blow-dry wave lotions, styling mousses, hair gels, hair waxes, or combinations thereof. In view of the fact that men in particular are often reluctant to use multiple different agents and/or multiple application steps, agents that men use already are preferred. Preferred agents are therefore shampoos, conditioning agents, or hair tonics.

The hair treatment agents contain, as a first essential ingredient, from about 0.001 to about 20 wt. % of at least one alpha-substituted aldehyde.

Preferred hair treatment agents as contemplated herein contain, based on their weight, from about 0.01 to about 10 wt. %, preferably from about 0.05 to about 7.5 wt. %, more preferably from about 0.1 to about 6 wt. %, and in particular from about 0.15 to about 5 wt. %, of alpha-substituted aldehyde(s) of formula (I)

Y—CH(X)—CHO    (I), in which

X represents —OH, —Cl, —Br, —I, —O—$(CH_2)_n$—$CH_3$ where n=1, 2, 3 or 4, or —O—$(CH_2)_m$—OH where m=1, 2 or 3;

Y represents —H, —$CH_3$, $H_3C$—$(CH_2)_k$— where k=1, 2, 3, 4, 5, 6, 7 or 8, —OH, —$(CH_2)_p$—OH where p=1, 2, 3 or 4, or —CHO.

Aldehydes which are preferably to be used as contemplated herein are, for example

| No. | X | Y |
|---|---|---|
| 1 | —OH | —H |
| 2 | —CL | —H |
| 3 | —Br | —H |
| 4 | —I | —H |
| 5 | $(CH_2)_n$—$CH_3$ | —H |
| 6 | $(CH_2)_n$—$CH_3$ | —H |
| 7 | $(CH_2)_n$—$CH_3$ | —H |
| 8 | $(CH_2)_4$—$CH_3$ | —H |
| 9 | $(CH_2)$—OH | —H |
| 10 | $(CH_2)_2$—OH | —H |
| 11 | $(CH_2)_3$—OH | —H |
| 12 | —OH | —$CH_3$ |
| 13 | —CL | —$CH_3$ |
| 14 | —Br | —$CH_3$ |
| 15 | —I | —$CH_3$ |
| 16 | —O—$(CH_2)_n$—$CH_3$ | —$CH_3$ |
| 17 | —O—$(CH_2)_n$—$CH_3$ | —$CH_3$ |
| 18 | —O—$(CH_2)_n$—$CH_3$ | —$CH_3$ |
| 19 | —O—$(CH_2)_4$—$CH_3$ | —$CH_3$ |
| 20 | —O—$(CH_2)$—OH | —$CH_3$ |
| 21 | —O—$(CH_2)_2$—OH | —$CH_3$ |
| 22 | —O—$(CH_2)_3$—OH | —$CH_3$ |
| 23 | —OH | —$(CH_2)$—$CH_3$ |
| 24 | —CL | —$(CH_2)$—$CH_3$ |
| 25 | —Br | —$(CH_2)$—$CH_3$ |
| 26 | —I | —$(CH_2)$—$CH_3$ |
| 27 | $(CH_2)_n$—$CH_3$ | —$(CH_2)$—$CH_3$ |
| 28 | $(CH_2)_n$—$CH_3$ | —$(CH_2)$—$CH_3$ |
| 29 | $(CH_2)_n$—$CH_3$ | —$(CH_2)$—$CH_3$ |
| 30 | $(CH_2)_4$—$CH_3$ | —$(CH_2)$—$CH_3$ |
| 31 | $(CH_2)$—OH | —$(CH_2)$—$CH_3$ |
| 32 | $(CH_2)_2$—OH | —$(CH_2)$—$CH_3$ |
| 33 | $(CH_2)_3$—OH | —$(CH_2)$—$CH_3$ |
| 34 | —OH | —$(CH_2)_2$—$CH_3$ |
| 35 | —CL | —$(CH_2)_2$—$CH_3$ |
| 36 | —Br | —$(CH_2)_2$—$CH_3$ |
| 37 | —I | —$(CH_2)_2$—$CH_3$ |
| 38 | —O—$(CH_2)_n$—$CH_3$ | —$(CH_2)_2$—$CH_3$ |
| 39 | —O—$(CH_2)_n$—$CH_3$ | —$(CH_2)_2$—$CH_3$ |
| 40 | —O—$(CH_2)_n$—$CH_3$ | —$(CH_2)_2$—$CH_3$ |
| 41 | —O—$(CH_2)_4$—$CH_3$ | —$(CH_2)_2$—$CH_3$ |
| 42 | —O—$(CH_2)$—OH | —$(CH_2)_2$—$CH_3$ |
| 43 | —O—$(CH_2)_2$—OH | —$(CH_2)_2$—$CH_3$ |
| 44 | —O—$(CH_2)_3$—OH | —$(CH_2)_2$—$CH_3$ |
| 45 | —OH | —$(CH_2)_3$—$CH_3$ |
| 46 | —CL | —$(CH_2)_3$—$CH_3$ |
| 47 | —Br | —$(CH_2)_3$—$CH_3$ |
| 48 | —I | —$(CH_2)_3$—$CH_3$ |
| 49 | —O—$(CH_2)_n$—$CH_3$ | —$(CH_2)_3$—$CH_3$ |
| 50 | —O—$(CH_2)_n$—$CH_3$ | —$(CH_2)_3$—$CH_3$ |
| 51 | —O—$(CH_2)_n$—$CH_3$ | —$(CH_2)_3$—$CH_3$ |
| 52 | —O—$(CH_2)_4$—$CH_3$ | —$(CH_2)_3$—$CH_3$ |
| 53 | —O—$(CH_2)$—OH | —$(CH_2)_3$—$CH_3$ |
| 54 | —O—$(CH_2)_2$—OH | —$(CH_2)_3$—$CH_3$ |
| 55 | —O—$(CH_2)_3$—OH | —$(CH_2)_3$—$CH_3$ |
| 56 | —OH | —$(CH_2)_4$—$CH_3$ |
| 57 | —CL | —$(CH_2)_4$—$CH_3$ |
| 58 | —Br | —$(CH_2)_4$—$CH_3$ |
| 59 | —I | —$(CH_2)_4$—$CH_3$ |
| 60 | —O—$(CH_2)_n$—$CH_3$ | —$(CH_2)_4$—$CH_3$ |
| 61 | —O—$(CH_2)_n$—$CH_3$ | —$(CH_2)_4$—$CH_3$ |
| 62 | —O—$(CH_2)_n$—$CH_3$ | —$(CH_2)_4$—$CH_3$ |
| 63 | —O—$(CH_2)_4$—$CH_3$ | —$(CH_2)_4$—$CH_3$ |
| 64 | —O—$(CH_2)$—OH | —$(CH_2)_4$—$CH_3$ |
| 65 | —O—$(CH_2)_2$—OH | —$(CH_2)_4$—$CH_3$ |
| 66 | —O—$(CH_2)_3$—OH | —$(CH_2)_4$—$CH_3$ |
| 67 | —OH | —$(CH_2)_5$—$CH_3$ |
| 68 | —CL | —$(CH_2)_5$—$CH_3$ |
| 69 | —Br | —$(CH_2)_5$—$CH_3$ |
| 70 | —I | —$(CH_2)_5$—$CH_3$ |
| 71 | —O—$(CH_2)_n$—$CH_3$ | —$(CH_2)_5$—$CH_3$ |
| 72 | —O—$(CH_2)_n$—$CH_3$ | —$(CH_2)_5$—$CH_3$ |
| 73 | —O—$(CH_2)_n$—$CH_3$ | —$(CH_2)_5$—$CH_3$ |
| 74 | —O—$(CH_2)_4$—$CH_3$ | —$(CH_2)_5$—$CH_3$ |
| 75 | —O—$(CH_2)$—OH | —$(CH_2)_5$—$CH_3$ |
| 76 | —O—$(CH_2)_2$—OH | —$(CH_2)_5$—$CH_3$ |
| 77 | —O—$(CH_2)_3$—OH | —$(CH_2)_5$—$CH_3$ |
| 78 | —OH | —$(CH_2)_6$—$CH_3$ |
| 79 | —CL | —$(CH_2)_6$—$CH_3$ |
| 80 | —Br | —$(CH_2)_6$—$CH_3$ |
| 81 | —I | —$(CH_2)_6$—$CH_3$ |
| 82 | —O—$(CH_2)_n$—$CH_3$ | —$(CH_2)_6$—$CH_3$ |
| 83 | —O—$(CH_2)_n$—$CH_3$ | —$(CH_2)_6$—$CH_3$ |
| 84 | —O—$(CH_2)_n$—$CH_3$ | —$(CH_2)_6$—$CH_3$ |
| 85 | —O—$(CH_2)_4$—$CH_3$ | —$(CH_2)_6$—$CH_3$ |
| 86 | —O—$(CH_2)$—OH | —$(CH_2)_6$—$CH_3$ |
| 87 | —O—$(CH_2)_2$—OH | —$(CH_2)_6$—$CH_3$ |
| 88 | —O—$(CH_2)_3$—OH | —$(CH_2)_6$—$CH_3$ |
| 89 | —OH | —$(CH_2)_7$—$CH_3$ |
| 90 | —CL | —$(CH_2)_7$—$CH_3$ |
| 91 | —Br | —$(CH_2)_7$—$CH_3$ |
| 92 | —I | —$(CH_2)_7$—$CH_3$ |
| 93 | —O—$(CH_2)_n$—$CH_3$ | —$(CH_2)_7$—$CH_3$ |
| 94 | —O—$(CH_2)_n$—$CH_3$ | —$(CH_2)_7$—$CH_3$ |
| 95 | —O—$(CH_2)_n$—$CH_3$ | —$(CH_2)_7$—$CH_3$ |
| 96 | —O—$(CH_2)_4$—$CH_3$ | —$(CH_2)_7$—$CH_3$ |
| 97 | —O—$(CH_2)$—OH | —$(CH_2)_7$—$CH_3$ |
| 98 | —O—$(CH_2)_2$—OH | —$(CH_2)_7$—$CH_3$ |
| 99 | —O—$(CH_2)_3$—OH | —$(CH_2)_7$—$CH_3$ |
| 100 | —OH | —$(CH_2)_8$—$CH_3$ |
| 101 | —CL | —$(CH_2)_8$—$CH_3$ |
| 102 | —Br | —$(CH_2)_8$—$CH_3$ |
| 103 | —I | —$(CH_2)_8$—$CH_3$ |
| 104 | —O—$(CH_2)_n$—$CH_3$ | —$(CH_2)_8$—$CH_3$ |
| 105 | —O—$(CH_2)_n$—$CH_3$ | —$(CH_2)_8$—$CH_3$ |
| 106 | —O—$(CH_2)_n$—$CH_3$ | —$(CH_2)_8$—$CH_3$ |
| 107 | —O—$(CH_2)_4$—$CH_3$ | —$(CH_2)_8$—$CH_3$ |
| 108 | —O—$(CH_2)$—OH | —$(CH_2)_8$—$CH_3$ |
| 109 | —O—$(CH_2)_2$—OH | —$(CH_2)_8$—$CH_3$ |
| 110 | —O—$(CH_2)_3$—OH | —$(CH_2)_8$—$CH_3$ |
| 111 | —OH | —OH |
| 112 | —CL | —OH |
| 113 | —Br | —OH |
| 114 | —I | —OH |
| 115 | —O—$(CH_2)_n$—$CH_3$ | —OH |
| 116 | —O—$(CH_2)_n$—$CH_3$ | —OH |
| 117 | —O—$(CH_2)_n$—$CH_3$ | —OH |
| 118 | —O—$(CH_2)_4$—$CH_3$ | —OH |
| 119 | —O—$(CH_2)$—OH | —OH |
| 120 | —O—$(CH_2)_2$—OH | —OH |
| 121 | —O—$(CH_2)_3$—OH | —OH |
| 122 | —OH | —$(CH_2)$—OH |
| 123 | —CL | —$(CH_2)$—OH |
| 124 | —Br | —$(CH_2)$—OH |
| 125 | —I | —$(CH_2)$—OH |
| 126 | —O—$(CH_2)_n$—$CH_3$ | —$(CH_2)$—OH |
| 127 | —O—$(CH_2)_n$—$CH_3$ | —$(CH_2)$—OH |

-continued

| No. | X | Y |
|---|---|---|
| 128 | —O—(CH$_2$)$_n$—CH$_3$ | —(CH$_2$)—OH |
| 129 | —O—(CH$_2$)$_4$—CH$_3$ | —(CH$_2$)—OH |
| 130 | —O—(CH$_2$)—OH | —(CH$_2$)—OH |
| 131 | —O—(CH$_2$)$_2$—OH | —(CH$_2$)—OH |
| 132 | —O—(CH$_2$)$_3$—OH | —(CH$_2$)—OH |
| 133 | —OH | —(CH$_2$)$_2$—OH |
| 134 | —CL | —(CH$_2$)$_2$—OH |
| 135 | —Br | —(CH$_2$)$_2$—OH |
| 136 | —I | —(CH$_2$)$_2$—OH |
| 137 | —O—(CH$_2$)$_n$—CH$_3$ | —(CH$_2$)$_2$—OH |
| 138 | —O—(CH$_2$)$_n$—CH$_3$ | —(CH$_2$)$_2$—OH |
| 139 | —O—(CH$_2$)$_n$—CH$_3$ | —(CH$_2$)$_2$—OH |
| 140 | —O—(CH$_2$)$_4$—CH$_3$ | —(CH$_2$)$_2$—OH |
| 141 | —O—(CH$_2$)—OH | —(CH$_2$)$_2$—OH |
| 142 | —O—(CH$_2$)$_2$—OH | —(CH$_2$)$_2$—OH |
| 143 | —O—(CH$_2$)$_3$—OH | —(CH$_2$)$_2$—OH |
| 144 | —OH | —(CH$_2$)$_3$—OH |
| 145 | —CL | —(CH$_2$)$_3$—OH |
| 146 | —Br | —(CH$_2$)$_3$—OH |
| 147 | —I | —(CH$_2$)$_3$—OH |
| 148 | —O—(CH$_2$)$_n$—CH$_3$ | —(CH$_2$)$_3$—OH |
| 149 | —O—(CH$_2$)$_n$—CH$_3$ | —(CH$_2$)$_3$—OH |
| 150 | —O—(CH$_2$)$_n$—CH$_3$ | —(CH$_2$)$_3$—OH |
| 151 | —O—(CH$_2$)$_4$—CH$_3$ | —(CH$_2$)$_3$—OH |
| 152 | —O—(CH$_2$)—OH | —(CH$_2$)$_3$—OH |
| 153 | —O—(CH$_2$)$_2$—OH | —(CH$_2$)$_3$—OH |
| 154 | —O—(CH$_2$)$_3$—OH | —(CH$_2$)$_3$—OH |
| 155 | —OH | —(CH$_2$)$_4$—OH |
| 156 | —CL | —(CH$_2$)$_4$—OH |
| 157 | —Br | —(CH$_2$)$_4$—OH |
| 158 | —I | —(CH$_2$)$_4$—OH |
| 159 | —O—(CH$_2$)$_n$—CH$_3$ | —(CH$_2$)$_4$—OH |
| 160 | —O—(CH$_2$)$_n$—CH$_3$ | —(CH$_2$)$_4$—OH |
| 161 | —O—(CH$_2$)$_n$—CH$_3$ | —(CH$_2$)$_4$—OH |
| 162 | —O—(CH$_2$)$_4$—CH$_3$ | —(CH$_2$)$_4$—OH |
| 163 | —O—(CH$_2$)—OH | —(CH$_2$)$_4$—OH |
| 164 | —O—(CH$_2$)$_2$—OH | —(CH$_2$)$_4$—OH |
| 165 | —O—(CH$_2$)$_3$—OH | —(CH$_2$)$_4$—OH |
| 166 | —OH | —CHO |
| 167 | —CL | —CHO |
| 168 | —Br | —CHO |
| 169 | —I | —CHO |
| 170 | —O—(CH$_2$)$_n$—CH$_3$ | —CHO |
| 171 | —O—(CH$_2$)$_n$—CH$_3$ | —CHO |
| 172 | —O—(CH$_2$)$_n$—CH$_3$ | —CHO |
| 173 | —O—(CH$_2$)$_4$—CH$_3$ | —CHO |
| 174 | —O—(CH$_2$)—OH | —CHO |
| 175 | —O—(CH$_2$)$_2$—OH | —CHO |
| 176 | —O—(CH$_2$)$_3$—OH | —CHO |

Very particularly preferred hair treatment agents as contemplated herein contain, based on their weight, from about 0.01 to about 10 wt. %, preferably from about 0.05 to about 7.5 wt. %, more preferably from about 0.1 to about 6 wt. %, and in particular from about 0.15 to about 5 wt. %, of at least one alpha-substituted aldehyde from the group 2-hydroxypropanal (X=—OH, Y=—CH$_3$):

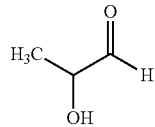

(Ia)

2-hydroxyhexanal (X=—OH, Y=H$_3$C—(CH$_2$)$_k$— where k=3):

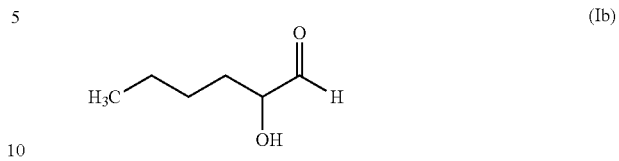

(Ib)

2-hydroxyoctanal (X=—OH, Y=H$_3$C—(CH$_2$)$_k$— where k=5):

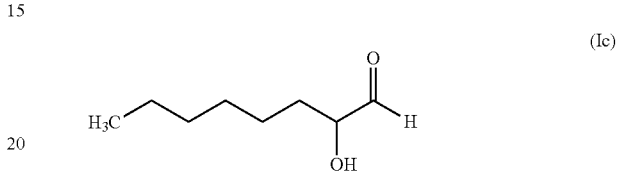

(Ic)

bromomalonaldehyde (X=Br, Y=—CH=):

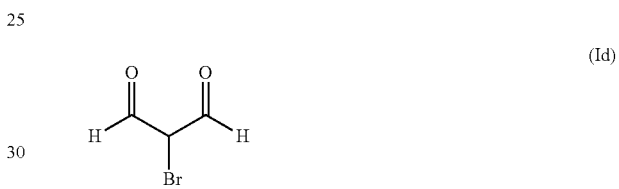

(Id)

2-(2-hydroxyethoxy)acetaldehyde (X=—O—(CH$_2$)$_p$—OH where p=2, Y=—H):

(Ie)

glyceraldehyde (X=—OH, Y=—(CH$_2$)$_p$—OH where p=1):

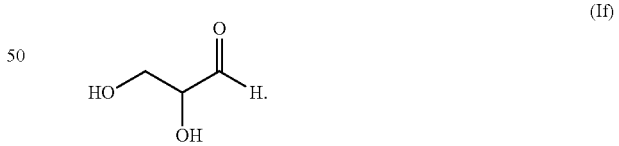

(If)

Hair treatment agents containing these aldehydes have excellent nourishing properties on both thin and normal hair, bring about significant structure strengthening and prevent washout and bleeding of chemically colored hair very effectively.

As further essential components, the agents as contemplated herein contain from about 0.001 to about 50 wt. % of at least one amino-functional silicone.

Preferred agents as contemplated herein contain an amino-functional silicone of formula (Si-II)

$$R'_aG_{3-a}\text{-Si}(OSiG_2)_n\text{-}(OSiG_bR'_{2-b})_m\text{—O—SiG}_{3-a}\text{-R'}_a \quad \text{(Si-II)},$$

in which:

G is —H, a phenyl group, —OH, —O—$CH_3$, —$CH_3$, —O—$CH_2CH_3$, —$CH_2CH_3$, —O—$CH_2CH_2CH_3$, —$CH_2CH_2CH_3$, —O—$CH(CH_3)_2$, —$CH(CH_3)_2$, —O—$CH_2CH_2CH_2CH_3$, —$CH_2CH_2CH_2CH_3$, —O—$CH_2CH(CH_3)_2$, —$CH_2CH(CH_3)_2$, —O—$CH(CH_3)CH_2CH_3$, —$CH(CH_3)CH_2CH_3$, —O—$C(CH_3)_3$, or —$C(CH_3)_3$;

a represents a number between 0 and about 3, in particular 0;

b represents a number between 0 and about 1, in particular about 1;

m and n are numbers whose sum (m+n) is between about 1 and about 2000, preferably between about 50 and about 150, n preferably assuming values of from 0 to about 1999 and in particular from about 49 to about 149 and m preferably assuming values of from about 1 to about 2000, in particular from about 1 to about 10;

R' is a monovalent functional group selected from
-Q-N(R")—$CH_2$—$CH_2$—N(R")$_2$
-Q-N(R")$_2$
-Q-N+(R")$_3$A$^-$
-Q-N+H(R")$_2$A$^-$
-Q-N+H$_2$(R")A$^-$
Q-N(R")—$CH_2$—$CH_2$—N$^+$R"H$_2$A$^-$, where each Q represents a chemical bond, —$CH_2$—, —$CH_2$—$CH_2$—, —$CH_2CH_2CH_2$—, —$C(CH_3)_2$—, —$CH_2CH_2CH_2CH_2$—, —$CH_2C(CH_3)_2$—, or —$CH(CH_3)CH_2CH_2$—, R" represents identical or different functional groups from the group —H, -phenyl, -benzyl, —$CH_2$—$CH(CH_3)Ph$, from the $C_{1-20}$ alkyl functional groups, preferably —$CH_3$, —$CH_2CH_3$, —$CH_2CH_2CH_3$, —$CH(CH_3)_2$, —$CH_2CH_2CH_2H_3$, —$CH_2CH(CH_3)_2$, —$CH(CH_3)CH_2CH_3$, —$C(CH_3)_3$, and A represents an anion preferably selected from chloride, bromide, iodide or methosulfate.

Particularly preferred agents as contemplated herein contain at least one amino-functional silicone of formula (Si-IIa)

(Si-IIa)
$(CH_3)_3Si—[O—Si(CH_3)_2]_n[OSi(CH_3)]_m—OSi(CH_3)_3$
                                    |
                                    $CH_2CH(CH_3)CH_3NH(CH_2)_2NH_2$, in which m and n are numbers whose sum (m+n) is between about 1 and about 2000, preferably between about 50 and about 150, n preferably assuming values of from 0 to about 1999 and in particular from about 49 to about 149 and m preferably assuming values of from about 1 to about 2000, in particular from about 1 to about 10.

These silicones are referred to as trimethylsilylamodimethicone according to the INCI declaration.

Particularly preferred as well are agents as contemplated herein that contain an amino-functional silicone of formula (Si-IIb)

(Si-IIb)
$R—[Si(CH_3)_2—O]_{n1}[Si(R)—O]_m—[Si(CH_3)_2]_{n2}—R$,
                          |
                          $(CH_2)_3NH(CH_2)_2NH_2$ in which R represents —OH, —O—$CH_3$, or a —$CH_3$ group and m, n1 and n2 are numbers whose sum (m+n1+n2) is between about 1 and about 2000, preferably between about 50 and about 150, the sum (n1+n2) preferably assuming values of from 0 to about 1999 and in particular from about 49 to about 149 and m preferably assuming values of from about 1 to about 2000, in particular from about 1 to about 10.

These silicones are referred to as amodimethicone according to the INCI declaration.

Irrespective of which amino-functional silicones are used, agents as contemplated herein are preferred that contain an amino-functional silicone of which the amine value is above about 0.25 meq/g, preferably above about 0.3 meq/g, and in particular above about 0.4 meq/g. The amine value here represents the milliequivalents of amine per gram of the amino-functional silicone. Said value can be determined by titration and may also be given in the unit mg KOH/g.

Hair treatment agents which are preferred as contemplated herein contain, based on their weight, from about 0.01 to about 20 wt. %, preferably from about 0.05 to about 10 wt. %, more preferably from about 0.1 to about 7.5 wt. %, and in particular from about 0.15 to about 5 wt. %, of amino-functional silicone(s).

The agents as contemplated herein particularly preferably contain amino-functional silicone(s) having terminal hydroxy group(s). Some special amino-functional silicone(s) having terminal hydroxy group(s) have been found to be particularly suitable in the agents as contemplated herein. These are described in the following.

Pretreatment agents that contain at least one silicone of formula (Si-V) have been found to be particularly effective in the method as contemplated herein with regard to the desired effects:

(Si-V)

$$A\!-\!\!\left[\!\!\begin{array}{c}CH_3\\|\\Si\!-\!\!O\\|\\CH_3\end{array}\!\!\right]_b\!\!\left[\!\!\begin{array}{c}CH_3\\|\\Si\!-\!\!O\\|\\\phantom{X}\end{array}\!\!\right]_n\!\!\left[\!\!\begin{array}{c}CH_3\\|\\Si\!-\!\!O\\|\\CH_3\end{array}\!\!\right]_c\!\!-\!D,$$

with pendant group: $HN\!\!-\!\!NH_2$ in which

A represents an —OH, —O—$Si(CH_3)_3$, —O—$Si(CH_3)_2OH$, or —O—$Si(CH_3)_2OCH_3$ group;

D represents an —H, —$Si(CH_3)_3$, —$Si(CH_3)_2OH$, or —$Si(CH_3)_2OCH_3$ group;

b, n and c represent integers between 0 and about 1,000, with the proviso that n>0 and b+c>0 at least one of the conditions A=—OH or D=—H is met.

Hair treatment agents as contemplated herein are therefore preferred as contemplated herein that contain, based on their weight, from about 0.01 to about 20 wt. %, preferably from about 0.01 to about 20 wt. %, more preferably from about 0.1 to about 10 wt. %, even more preferably from about 0.5 to about 7.5 wt. %, and in particular from about 0.1 to about 5 wt. %, of at least one silicone of formula (Si-V):

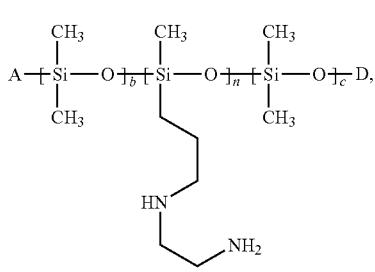

(Si-V)

in which
A represents an —OH, —O—Si(CH₃)₃, —O—Si(CH₃)₂OH, or —O—Si(CH₃)₂OCH₃ group;
D represents an —H, —Si(CH₃)₃, —Si(CH₃)₂OH, or —Si(CH₃)₂OCH₃ group;
b, n and c represent integers between 0 and about 1,000, with the proviso that
n>0 and b+c>0
at least one of the conditions A=—OH or D=—H is met.

In the above formula (Si-V), the individual siloxane units having the indices b, c and n are randomly distributed, i.e. they are not necessarily block copolymers.

Further particularly suitable silicones are 4-morpholinomethyl-substituted. Hair treatment agents as contemplated herein are particularly preferred that contain, based on their weight, from about 0.001 to about 20 wt. %, preferably from about 0.01 to about 10 wt. %, particularly preferably from about 0.05 to about 7.5 wt. %, and in particular from about 0.5 to about 5 wt. %, of at least one 4-morpholinomethyl-substituted silicone which comprises structural units of formulas (Si-VIa), (Si-VIb) and (Si-VIc)

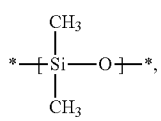

(Si-VIa)

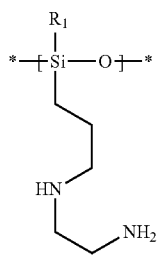

(Si-VIb)

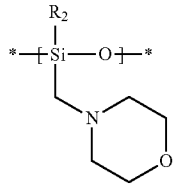

(Si-VIc)

(Si-VI), in which
R1 represents —CH₃, —OH, —OCH₃, —O—CH₂CH₃, —O—CH₂CH₂CH₃, or —O—CH(CH₃)₂;
R2 represents —CH₃, —OH, or —OCH₃.

Particularly preferred hair treatment agents as contemplated herein contain, based on their weight, from about 0.001 to about 20 wt. %, preferably from about 0.01 to about 10 wt. %, particularly preferably from about 0.05 to about 7.5 wt. %, and in particular from about 0.5 to about 5 wt. %, of at least one 4-morpholinomethyl-substituted silicone of formula (Si-VI)

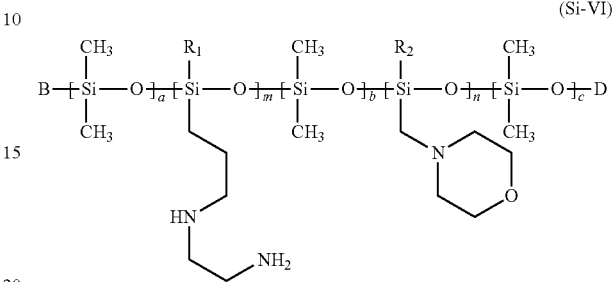

(Si-VI)

in which
R1 represents —CH₃, —OH, —OCH₃, —O—CH₂CH₃, —O—CH₂CH₂CH₃, or —O—CH(CH₃)₂;
R2 represents —CH₃, —OH, or —OCH₃;
B represents an —OH, —O—Si(CH₃)₃, —O—Si(CH₃)₂OH, or —O—Si(CH₃)₂OCH₃ group;
D represents an —H, —Si(CH₃)₃, —Si(CH₃)₂OH, or —Si(CH₃)₂OCH₃ group;
a, b and c represent, independently of one another, integers between 0 and about 1,000, with the proviso that a+b+c>0;
m and n represent, independently of one another, integers between about 1 and about 1,000 with the proviso that at least one of the conditions B=—OH or D=—H is met,
the units a, b, c, m and n are distributed randomly or in blocks in the molecule.

Structural formula (Si-VI) is intended to indicate that the siloxane groups n and m do not necessarily have to be directly bonded to an end group B or D. Instead, in preferred formulas (Si-VI), a>0 or b>0 and, in particularly preferred formulas (Si-VI), a>0 and c>0; i.e., the terminal group B or D is preferably bound to a dimethylsiloxy group. In formula (Si-VI) as well, the siloxane units a, b, c, m and n are preferably distributed randomly.

The silicones represented by formula (Si-VI) and used as contemplated herein can be trimethylsilyl-terminated (D or B=—Si(CH₃)₃), but they may also be dimethylsilylhydroxy-terminated at both ends or dimethylsilylhydroxy-terminated at one end and dimethylsilylmethoxy-terminated at the other end. In the context of the present disclosure, silicones used particularly preferably are selected from silicones in which
B=—O—Si(CH₃)₂OH and D=—Si(CH₃)₃
B=—O—Si(CH₃)₂OH and D=—Si(CH₃)₂OH
B=—O—Si(CH₃)₂OH and D=—Si(CH₃)₂OCH₃
B=—O—Si(CH₃)₃ and D=—Si(CH₃)₂OH
B=—O—Si(CH₃)₂OCH₃ and D=—Si(CH₃)₂OH.

These silicones lead to enormous improvements in the hair properties of hair treated with the agents as contemplated herein, and to greatly improved protection during oxidative treatment.

Irrespective of the type of amino-functional silicone(s) having terminal hydroxy group(s) used, the agents as contemplated herein contain the silicone(s) preferably in the form of an emulsion, particularly preferably in the form of a microemulsion.

It has been found that the effect of the silicones used in the agents as contemplated herein can be increased further still if certain nonionic components are also used in the agents. In addition, these nonionic components have positive effects on the storage stability of the agents. Nonionic components that are particularly suitable here are ethoxylates of decanol, undecanol, dodecanol, tridecanol, etc. Ethoxylated tridecanols which are particularly preferably incorporated in the agents as contemplated herein have been found to be particularly suitable. Agents which are particularly preferred as contemplated herein contain, based on their weight, from about 0.00001 to about 5 wt. %, preferably from about 0.0001 to about 3.5 wt. %, particularly preferably from about 0.001 to about 2 wt. %, more preferably from about 0.01 to about 1 wt. %, and in particular from about 0.1 to about 0.5 wt. %, of branched ethoxylated tridecanol (INCI name: trideceth-5) or α-iso-tridecyl-ω-hydroxy polyglycol ether (INCI name: trideceth-10) or mixtures thereof.

In addition to the amino-functional silicone(s), the agents as contemplated herein may contain further silicone(s) which is/are not amino-functional.

The hair treatment agents as contemplated herein may contain surfactant(s). In cleaning compositions (shampoos), in particular anionic surfactants have been found to be suitable and, in conditioning compositions, cationic surfactants are ingredients that are often used; owing to their advantageous properties, amphoteric surfactants are particularly preferably used in both shampoos and conditioners.

The hair treatment agents as contemplated herein may contain at least one anionic surfactant.

Suitable anionic surfactants and emulsifiers for the compositions as contemplated herein include all anionic surface-active substances suitable for use on the human body. These are exemplified by a water-solubilizing, anionic group such as a carboxylate, sulfate, sulfonate or phosphate group and a lipophilic alkyl group having approximately 8 to about 30 C atoms. In addition, glycol or polyglycol ether groups, ester, ether and amide groups, and hydroxyl groups, may additionally be contained in the molecule.

Preferred hair treatment agents contain, based on their weight, from about 0.5 to about 20 wt. %, preferably from about 0.75 to about 15 wt. %, more preferably from about 1 to about 12 wt. %, and in particular from about 2 to about 10 wt. %, of anionic surfactant(s).

Particularly preferred hair treatment agents as contemplated herein contain, based on their weight, from about 0.5 to about 20 wt. %, preferably from about 0.75 to about 15 wt. %, more preferably from about 1 to about 12 wt. %, and in particular from about 2 to about 10 wt. %, of alkyl (ether) sulfates of general formula R—(OCH$_2$—CH$_2$)$_n$—OSO$_3$X, in which R is a straight-chain or branched, saturated or unsaturated alkyl group having 8 to 24 C atoms, n is the number 0 or from about 1 to about 12, and X is an alkali, alkaline-earth, ammonium or alkanolamine ion.

The hair treatment agents as contemplated herein may contain at least one amphoteric surfactant and/or at least one nonionic surfactant.

Particularly preferred hair treatment agents as contemplated herein contain, based on their weight, from about 0.3 to about 20 wt. %, preferably from about 0.5 to about 8 wt. %, more preferably from about 0.75 to about 6 wt. %, and in particular from about 1 to about 5 wt. %, of amphoteric surfactant(s). Surfactants that have both a negatively-charged functional group and a positively-charged functional group are referred to as amphoteric surfactants or zwitterionic surfactants.

Particularly suitable zwitterionic surfactants are what are referred to as betaines, such as N-alkyl-N,N-dimethylammonium glycinates, for example cocoalkyl dimethylammonium glycinate, N-acylaminopropyl-N,N-dimethylammonium glycinates, for example cocoacylaminopropyl dimethylammonium glycinate, 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known by the INCI name cocamidopropyl betaine.

The hair treatment agents may contain nonionic surfactant(s).

Hair treatment agents which are preferred as contemplated herein contain, based on their weight, from about 0.3 to about 10 wt. %, preferably from about 0.5 to about 8 wt. %, more preferably from about 0.75 to about 6 wt. %, and in particular from about 1 to about 5 wt. %, of nonionic surfactant(s).

The hair treatment agents may contain cationic surfactant(s). As contemplated herein, it is possible to use cationic surfactants of the following types: quaternary ammonium compounds, esterquats, and amidoamines. Preferred quaternary ammonium compounds are ammonium halides, in particular chlorides and bromides, such as alkyl trimethylammonium chlorides, dialkyl dimethylammonium chlorides, and trialkyl methylammonium chlorides. The long alkyl chains of these surfactants preferably have about 10 to about 18 carbon atoms, such as in cetyl trimethylammonium chloride, stearyl trimethylammonium chloride, distearyl dimethylammonium chloride, lauryl dimethylammonium chloride, lauryl dimethylbenzylammonium chloride, and tricetyl methylammonium chloride. Further preferred cationic surfactants are the imidazolium compounds known by the INCI names quaternium-27 and quaternium-83.

Particularly preferred hair treatment agents as contemplated herein contain as the cationic care substance, based on their weight, from about 0.05 to about 7.5 wt. %, preferably from about 0.1 to about 5 wt. %, particularly preferably from about 0.2 to about 3.5 wt. %, and in particular from about 0.25 to about 2.5 wt. %, of cationic surfactant(s) from the group of quaternary ammonium compounds and/or esterquats and/or amidoamines.

Particularly preferred hair treatment agents as contemplated herein contain, based on the weight of the agent, from about 0.05 to about 20 wt. %, preferably from about 0.1 to about 10 wt. %, more preferably from about 0.25 to about 8 wt. %, and in particular from about 0.5 to about 7 wt. %, of cationic surfactant(s), and preferably from about 0.05 wt. % to about 20 wt. %, more preferably from about 0.1 to about 10 wt. %, even more preferably from about 0.25 to about 8 wt. %, and in particular from about 0.5 to about 7 wt. %, of behenyl trimethyl ammonium chloride.

The agents as contemplated herein may contain at least one cationic polymer.

Cationic polysaccharide polymers increase the nourishing performance of the hair treatment agents as contemplated herein (in particular the efficacy of the agents as contemplated herein with respect to hair breakage). Suitable cationic polysaccharide polymers may be selected from cationic cellulose compounds and/or from cationic guar derivatives.

Particularly preferred hair treatment agents as contemplated herein contain as cationic polysaccharide polymer(s), based on the weight of the agent, from about 0.01 to about 3 wt. %, preferably from about 0.05 to about 2 wt. %, more preferably from about 0.1 to about 1.5 wt. %, and in particular from about 0.15 to about 0.8 wt. %, of at least one polymer from the group of cationic cellulose polymers and/or cationic guar derivatives.

Cationic cellulose compounds within the meaning of the present disclosure are those that carry more than one permanent cationic charge in at least one side chain. Cellulose is constructed from beta-1,4-glycosidically linked D-glucopyranose units and forms unbranched, water-insoluble chains. A "side chain" of a cellulose defines chemical substituents which bind to the cellulose backbone and are not part of the native cellulose, since they have been introduced subsequently, for example by chemical synthesis.

Quaternized cellulose polymers originating from hydroxy ($C_2$-$C_4$)alkyl celluloses, particularly preferably from hydroxyethyl celluloses, are preferred.

Polymers of this kind are known to a person skilled in the art and are commercially available from various companies. The cationic cellulose derivatives known by the INCI names polyquaternium-4, polyquaternium-10, polyquaternium-24, polyquaternium-67, and/or polyquaternium-72 are particularly preferred. Polyquaternium-10, polyquaternium-24, and/or polyquaternium-67 are very particularly preferred, with polyquaternium-10 being particularly preferred.

Preferred hair treatment agents as contemplated herein contain as cationic polysaccharide polymer(s), based on the weight of the agent, from about 0.01 to about 3 wt. %, preferably from about 0.05 to about 2 wt. %, more preferably from about 0.1 to about 1.5 wt. %, and in particular from about 0.15 to about 0.8 wt, %, of at least one polymer from the group of polyquaternium-4, polyquaternium-10, polyquaternium-24, polyquaternium-67, and/or polyquaternium-72.

Particularly preferred hair treatment agents as contemplated herein contain as cationic polysaccharide polymer(s), based on the weight of the agent, from about 0.01 to about 3 wt. %, preferably from about 0.05 to about 2 wt. %, more preferably from about 0.1 to about 1.5 wt. %, and in particular from about 0.15 to about 0.8 wt. %, of polyquaternium-10.

Suitable cationic guar derivatives within the meaning of the present disclosure are cationic hydroxyalkyl guar derivatives, preferably cationic hydroxyethyl trimethylammonium guar and/or cationic hydroxypropyl trimethylammonium guar having average molecular weights between about 100,000 and about 2,000,000 daltons. The cationic guar polymers known by the INCI name guar hydroxypropyltrimonium chloride having a molecular weight (weight average) between about 200,000 and about 1,600,000 daltons are particularly preferred. The cationic charge density of these guar polymers is preferably at least about 0.4 meq/g, preferably at least about 0.5 meq/g, and in particular at least about 0.6 meq/g. Their nitrogen content is preferably in a range of from about 1.1 to about 1.8 wt. % (based on their total weight).

Cationic guar derivatives known by the INCI name guar hydroxypropyltrimonium chloride are known to a person skilled in the art and are obtainable for example under the trade names Cosmedia® Guar, N-Hance® and/or Jaguar® from various providers.

Particularly preferred hair treatment agents as contemplated herein contain as cationic polysaccharide polymer(s), based on the weight of the agent, from about 0.01 to about 3 wt. %, preferably from about 0.05 to about 2 wt. %, more preferably from about 0.1 to about 1.5 wt. %, and in particular from about 0.15 to about 0.8 wt. %, of guar hydroxypropyltrimonium chloride.

In summary, hair treatment agents which are preferred as contemplated herein contain, based on the weight of the agent, from about 0.01 to about 3 wt. %, preferably from about 0.05 to about 2 wt. %, more preferably from about 0.1 to about 1.5 wt. %, and in particular from about 0.15 to about 0.8 wt. %, of cationic polymer(s), and preferably from about 0.01 wt. % to about 3 wt. %, more preferably from about 0.05 to about 2 wt. %, even more preferably from about 0.1 to about 1.5 wt. %, and in particular from about 0.15 to about 0.8 wt. %, of at least one polymer from the group of cationic cellulose polymers and/or cationic guar derivatives.

It has been found that succinimidyl esters can further enhance the effect of the agents as contemplated herein. In particular, significant increases in performance are observed with regard to the inner structural strengthening of keratin fibers and the prevention of washout.

Hair treatment agents which are preferred as contemplated herein additionally contain, based on the weight of the agent, from about 0.001 to about 10 wt. % of at least one succinimidyl ester.

Succinimidyl esters are esters of carboxylic acids having (optionally substituted) N-hydroxysuccinimide (NHS, IUPAC 1-hydroxy-2,5-pyrrolidinedione) and are also referred to as NHS esters. Hair treatment agents which are preferred as contemplated herein additionally contain, based on the weight of the agent, from about 0.01 to about 10 wt. %, preferably from about 0.05 to about 7.5 wt. %, more preferably from about 0.1 to about 6 wt. %, and in particular from about 0.15 to about 5 wt. %, of (a) succinimidyl ester(s) of formula (III)

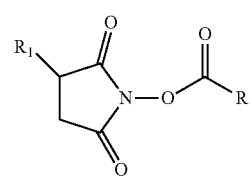

in which
R1 represents —H or an ionic group;
R represents an optionally substituted saturated or unsaturated, linear, branched or cyclic, aliphatic or aromatic hydrocarbon functional group having at least 5 C atoms.

Suitable ionic groups R1 include both anionic groups such as phosphate, phosphonate, phosphinate, sulfate, sulfonate, sulfinate, sulfenate, oxysulfonate, carboxylate groups and cationic groups such as substituted or unsubstituted ammonium groups. Zwitterionic/betainic groups such as carboxybetaine or sulfobetaine groups are also possible.

In succinimidyl esters which are preferred as contemplated herein, R1 represents —H, —$OSO_3^-$, —$SO_3^-$, —$SO_2^-$, —$COO^-$, —$NH_3^+$, —$N(CH_3)H_2^+$, —$N(CH_3)_2H^+$, —$N(CH_3)_3^+$, —$N^+(CH_3)_2(CH_2)_2$—$COO^-$, or —$N^+(CH_3)_2(CH_2)_3$—$SO_3^-$.

Succinimidyl esters that are preferably to be used as contemplated herein are described on pages 32 to 35 of the priority document as numbers 1 to 72.

Very particularly preferred hair treatment agents as contemplated herein contain, based on their weight, from about 0.01 to about 10 wt. %, preferably from about 0.05 to about 7.5 wt. %, more preferably from about 0.1 to about 6 wt. %, and in particular from about 0.15 to about 5 wt. %, of at least one succinimidyl ester from the group

(IIIa)

in which R represents -Ph or —(CH$_2$)nCH$_3$ where n=4, 5, 6, 7, 8, 9 or 10,

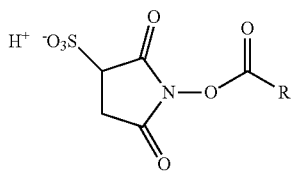

(IIIb)

in which R represents -Ph or —(CH$_2$)nCH$_3$ where n=4, 5, 6, 7, 8, 9 or 10 and
X represents H, a monovalent cation or the n-th part of an n-valent cation,

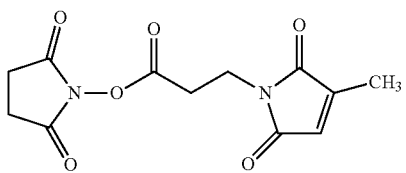

(IIIc)

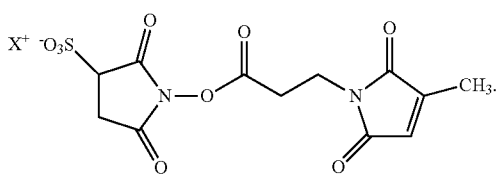

(IIId)

Complexing agents can further increase the effect of the agents as contemplated herein, complexing agents which are derived from polycarboxylic acids having been found to be particularly suitable.

Hair treatment agents which are preferred as contemplated herein contain, based on their weight, from about 0.001 to about 20 wt. % of complexing agents from the group tetrasodium-N,N-bis(carboxylatomethyl)-L-glutamate (tetrasodium glutamate diacetate, GLDA), pentasodium diethylenetriaminepentaacetate (DTPA), tetrasodium iminodisuccinate (IDS), tetrasodium ethylenediaminetetraacetate (EDTA), tetrasodium ethylenediamine disuccinic acid (EDDS), or trisodium hydroxyethyl ethylenediaminetriaccetic acid (HEDTA).

The use of the three complexing agents mentioned first is very particularly preferred. Extremely preferred hair treatment agents as contemplated herein contain, based on their weight, from about 0.001 to about 20 wt. %, preferably from about 0.005 to about 15 wt. %, more preferably from about 0.01 to about 10 wt. %, even more preferably from about 0.05 to about 7.5 wt. %, and in particular from about 0.1 to about 5 wt. %, of complexing agents from the group a. tetrasodium-N,N-bis(carboxylatomethyl)-L-glutamate (tetrasodium glutamate diacetate, GLDA),
b. pentasodium diethylenetriaminepentaacetate (DTPA),
c. tetrasodium iminodisuccinate (IDS).

The agents as contemplated herein may contain only one of the three complexing agents mentioned. However, it is also possible for the agents as contemplated herein to contain two or all three of the above-mentioned complexing agents, the amount of all the complexing agents from the above-mentioned group contained in the agents being within an amount range of from about 0.01 to about 20 wt. %.

Hair treatment agents which are preferred as contemplated herein contain, based on their weight, from about 0.005 to about 15 wt. %, preferably from about 0.01 to about 10 wt. %, more preferably from about 0.05 to about 7.5 wt. %, and in particular from about 0.1 to about 5 wt. %, of tetrasodium-N,N-bis(carboxylatomethyl)-L-glutamate (tetrasodium glutamate diacetate, GLDA).

Hair treatment agents which are also preferred as contemplated herein contain, based on their weight, from about 0.005 to about 15 wt. %, preferably from about 0.01 to about 10 wt. %, more preferably from about 0.05 to about 7.5 wt. %, and in particular from about 0.1 to about 5 wt. %, of pentasodium diethylenetriaminepentaacetate (DTPA).

Hair treatment agents which are also preferred as contemplated herein contain, based on their weight, from about 0.005 to about 15 wt. %, preferably from about 0.01 to about 10 wt. %, more preferably from about 0.05 to about 7.5 wt. %, and in particular from about 0.1 to about 5 wt. %, of tetrasodium iminodisuccinate (IDS).

Hair treatment agents which are also preferred as contemplated herein contain, based on their weight, from about 0.01 to about 10 wt. %, more preferably from about 0.05 to 7.5 wt. %, and in particular from about 0.1 to about 5 wt. %, of tetrasodium-N,N-bis(carboxylatomethyl)-L-glutamate (tetrasodium glutamate diacetate, GLDA), and from about 0.01 to about 10 wt. %, more preferably from about 0.05 to about 7.5 wt. %, and in particular from about 0.1 to about 5 wt. %, of pentasodium diethylenetriaminepentaacetate (DTPA).

Hair treatment agents which are also preferred as contemplated herein contain, based on their weight, from about 0.01 to about 10 wt. %, more preferably from about 0.05 to about 7.5 wt. %, and in particular from about 0.1 to about 5 wt. %, of tetrasodium-N,N-bis(carboxylatomethyl)-L-glutamate (tetrasodium glutamate diacetate, GLDA), and from about 0.01 to about 10 wt. %, more preferably from about 0.05 to about 7.5 wt. %, and in particular from about 0.1 to about 5 wt. %, of tetrasodium iminodisuccinate (IDS).

Hair treatment agents which are also preferred as contemplated herein contain, based on their weight, from about 0.01 to about 10 wt. %, more preferably from about 0.05 to about 7.5 wt. %, and in particular from about 0.1 to about 5 wt. %, of pentasodium diethylenetriaminepentaacetate (DTPA), and from about 0.01 to about 10 wt. %, more preferably from about 0.05 to about 7.5 wt. %, and in particular from about 0.1 to about 5 wt. %, of tetrasodium iminodisuccinate (IDS).

Hair treatment agents which are also preferred as contemplated herein contain, based on their weight, from about 0.1 to about 5 wt. % of tetrasodium-N,N-bis(carboxylatomethyl)-L-glutamate (tetrasodium glutamate diacetate, GLDA), from about 0.1 to about 5 wt. % of pentasodium diethylenetriaminepentaacetate (DTPA), and from about 0.1 to about 5 wt. % of tetrasodium iminodisuccinate (IDS).

The hair treatment agents may contain at least one bivalent or trivalent metal salt. These lead to improved washout prevention. To achieve an optimum effect, it is advantageous for the metal salts to be present in dissolved form in the agents as contemplated herein. In a preferred embodiment, the hair cleaning and care agents as contemplated herein therefore contain water-soluble bivalent or trivalent metal salts. "Water-soluble" is understood here to mean that, at about 20° C., at least about 1 g of the salt in question can dissolve fully in about 1 L of water.

Suitable divalent or trivalent metal salts may be selected from divalent or trivalent organic and/or inorganic salts.

Particularly suitable cations within these salts may preferably be selected from alkaline-earth metal cations and from copper, zinc, iron(II), iron(III), and/or aluminum cations. Alkaline-earth metal cations, and particularly preferably calcium and magnesium cations, are very particularly preferred. Particularly suitable organic anions within these salts may preferably be selected from formate, acetate, lactate, succinate, citrate, tartrate, malate, maleate, oxalate, and/or glycolate ions. Acetate, lactate, and/or citrate salts having the aforementioned cations are very particularly preferred.

Particularly preferred organic salts are calcium lactate, calcium citrate, calcium acetate, magnesium lactate, magnesium citrate, and/or magnesium acetate.

Particularly suitable inorganic anions within these salts may be selected from halide, sulfate, phosphate, and/or carbonate ions. Sulfate and/or halide ions such as chloride and bromide ions are very particularly preferred.

Particularly preferred inorganic salts are calcium chloride, calcium sulfate, magnesium chloride, and/or magnesium sulfate.

The weight proportion of the at least one bivalent or trivalent metal salt in terms of the total weight of the hair treatment agents as contemplated herein is preferably from about 0.01 to about 10 wt. %, more preferably from about 0.1 to about 7.5 wt. %, even more preferably from about 0.2 to about 5 wt. %, and in particular from about 0.3 to about 3 wt. %.

Hair treatment agents which are preferred as contemplated herein contain, based on their weight, from about 0.01 to about 10 wt. %, preferably from about 0.1 to about 7.5 wt. %, more preferably from about 0.2 to about 5 wt. %, and in particular from about 0.3 to about 3 wt. %, of at least one bivalent or trivalent metal salt from the group of organic or inorganic copper, zinc, iron(II), calcium, magnesium, iron (III), and/or aluminum salts.

Water-soluble salts are particularly preferred in this embodiment. Calcium lactate, calcium citrate, calcium acetate, magnesium lactate, magnesium citrate, magnesium acetate, calcium halides, calcium hydroxide, magnesium halides, and/or magnesium hydroxide are very particularly preferred in this embodiment.

The hair treatment agents contain the above-described active ingredients preferably in a cosmetically acceptable carrier. Within the context of the present disclosure, this is understood to preferably mean an aqueous or aqueous-alcoholic carrier.

The cosmetic carrier preferably contains at least about 50 wt. %, more preferably at least about 60 wt. %, particularly preferably at least about 70 wt. %, and more particularly preferably at least about 75 wt. %, of water.

Furthermore, the cosmetic carrier may contain from about 0.01 to about 40 wt. %, preferably from about 0.05 to about 30 wt. %, and in particular from about 0.1 to about 20 wt. %, of at least one alcohol.

Suitable alcohols are, for example, ethanol, ethyl diglycol, 1-propanol, 2-propanol, isopropanol, 1,2-propylene glycol, glycerol, diglycerol, triglycerol, 1-butanol, 2-butanol, 1,2-butanediol, 1,3-butanediol, 1-pentanol, 2-pentanol, 1,2-pentanediol, 1,5-pentanediol, 1-hexanol, 2-hexanol, 1,2-hexanediol, 1,6-hexanediol, polyethylene glycols, sorbitol, sorbitan, benzyl alcohol, or mixtures of said alcohols.

Water-soluble alcohols are particularly preferred. Ethanol, 1,2-propylene glycol, glycerol, benzyl alcohol, and mixtures of said alcohols are particularly preferred.

It is advantageous for very good (scalp) skin compatibility of the hair treatment agents as contemplated herein if said agents have a slightly acidic pH.

It has been found that the agents as contemplated herein have particularly good skin compatibility and mildness in a pH range of from about 4.2 to about 5.8.

In a first preferred embodiment, the hair treatment agents as contemplated herein therefore preferably have a pH in the range of from about 4.2 to about 5.8, more preferably from about 4.3 to about 5.6, particularly preferably from about 4.4 to about 5.5, extremely preferably from about 4.5 to about 5.4, and particularly preferably from about 4.7 to about 5.3.

The hair treatment agents as contemplated herein may contain vegetable oils, vegetable butters, and/or vegetable waxes. These vegetable oil components give the hair improved combability and stylability and increase hair shine.

Suitable vegetable oil components include natural (vegetable) oils and/or butters which typically contain triglycerides and mixtures of triglycerides.

Preferred natural oils are coconut oil, (sweet) almond oil, walnut oil, peach kernel oil, apricot kernel oil, argan oil, avocado oil, tea tree oil, soybean oil, sesame oil, sunflower oil, tsubaki oil, evening primrose oil, rice bran oil, palm kernel oil, mango kernel oil, marula oil, cuckoo flower oil, thistle oil, macadamia nut oil, grape seed oil, amaranth seed oil, bamboo oil, olive oil, wheat germ oil, pumpkin seed oil, mallow oil, hazelnut oil, safflower oil, canola oil, sasanqua oil, jojoba oil, rambutan oil, cocoa butter, and/or shea butter.

Carnauba wax, beeswax, and/or candelilla wax can preferably be used as suitable natural or vegetable waxes.

Particularly preferred vegetable oil components are (sweet) almond oil, peach kernel oil, apricot kernel oil, amaranth seed oil, argan oil, olive oil, jojoba oil, cocoa butter, and/or shea butter.

The weight proportion of the at least one vegetable oil, vegetable butter, and/or vegetable wax in terms of the total weight of the hair treatment agents as contemplated herein is preferably from about 0.02 to about 2.50 wt. %, more preferably from about 0.03 to about 2.00 wt. %, particularly preferably from about 0.04 to about 1.50 wt. %, and in particular from about 0.05 to about 1.00 wt. %.

In addition to the aforementioned essential and optional components, the hair treatment agents as contemplated herein may contain, in a further preferred embodiment for further increasing the nourishing properties of the agents, at least one further active hair-conditioning ingredient, which can be selected from the group of protein hydrolyzates,
vitamins,
plant extracts, and/or
glycerol.

Vitamins, provitamins, and vitamin precursors from the groups A, B, E, and H are particularly preferred. Particularly preferred are nicotinamide, biotin, pantolactone, and/or panthenol.

The weight proportion of the vitamin(s), vitamin derivative(s), and/or vitamin precursor(s) in terms of the total weight of the hair treatment agents is preferably from about 0.001 to about 2 wt. %, particularly preferably from about 0.005 to about 1 wt. %, and in particular from about 0.01 to about 0.5 wt. %.

Suitable plant extracts are to be understood to mean extracts that can be prepared from all parts of a plant. These extracts are typically prepared by extraction of the entire plant. It may also be preferable in individual cases, however, to prepare the extracts solely from the flowers and/or leaves of the plant. Particularly suitable are the extracts from green tea, oak bark, stinging nettle, witch hazel, hops, chamomile, burdock root, horsetail, whitethorn, lime blossom, lychee, almond, aloe vera, pine needles, horse chestnut, sandalwood, juniper, coconut, mango, apricot, lemon, wheat, kiwi, melon, orange, grapefruit, sage, rosemary, birch, mallow, cuckoo flower, wild thyme, yarrow, thyme, melissa, restharrow, coltsfoot, marshmallow, *ginseng*, ginger root, *Echinacea purpurea, Olea europaea, Boerhavia diffusa* roots, *Foeniculum vulgaris*, and *Apium graveolens*.

The extracts from green tea, stinging nettle, witch hazel, chamomile, aloe vera, *ginseng, Echinacea purpurea, Olea europaea*, and/or *Boerhavia diffusa* roots are particularly preferred for use in the compositions as contemplated herein.

Water, alcohols, and mixtures thereof can be used as extracting agents for preparing the mentioned plant extracts. Of the alcohols, low alcohols such as ethanol and isopropanol, but in particular polyhydric alcohols such as ethylene glycol and propylene glycol, are preferred, both as the sole extracting agent and in a mixture with water. Plant extracts based on water/propylene glycol in a ratio of from about 1:10 to about 10:1 have been found to be particularly suitable.

The plant extracts can be used both in pure and diluted form. If they are used in diluted form, they typically contain approximately 2 to about 80 wt. % of active substance and the extraction agent or extraction agent mixture used for their extraction as the solvent.

The plant extracts can be used in the hair treatment agents as contemplated herein (based on the total weight of the agents) preferably in an amount of from about 0.01 to about 10 wt. %, more preferably from about 0.05 to about 7.5 wt. %, and in particular from about 0.1 to about 5 wt. %.

Glycerol can be added to the hair cleaning and care agents separately in an amount of up to about 10 wt. % (based on the total weight of the agent). However, it may also be a component of the above-mentioned aqueous-alcoholic carrier.

It has been found that the hair treatment agents as contemplated herein are also suitable for use as an anti-dandruff preparation.

The total weight of anti-dandruff agents in terms of the total weight of the hair treatment agents can preferably be from about 0.01 to about 10 wt. %, more preferably from about 0.025 to about 7.5 wt. %, particularly preferably from about 0.05 to about 5 wt. %, and in particular from about 0.075 to about 3 wt. %.

Suitable anti-dandruff active ingredients can be selected from piroctone olamine, climbazole, zinc pyrithione, ketoconazole, salicylic acid, sulfur, selenium sulfide, tar preparations, undecenoic acid derivatives, burdock root extracts, poplar extracts, stinging nettle extracts, walnut shell extracts, birch extracts, willow bark extracts, rosemary extracts, and/or *arnica* extracts.

Climbazole, zinc pyrithione, and piroctone olamine are preferred.

The agents as contemplated herein can be formulated as what are referred to as rinse-off products, i.e. are rinsed out of the hair again after a specific contact time. This contact time is preferably less than an hour, i.e. the consumer preferably does not leave the products in the hair until the next time the hair is washed.

A further subject of the present disclosure is therefore a method for treating hair in which an agent as contemplated herein is applied to dry or wet hair, is left there for a period of from about 10 to about 300 seconds, and is rinsed out thereafter.

The agents as contemplated herein can also be formulated as what are referred to as leave-on products, i.e. are not rinsed out of the hair, but are instead left there until the next time the hair is washed. A further subject of the present disclosure is therefore a method for treating hair in which an agent as contemplated herein is applied to dry or wet hair and is left there until the next time the hair is washed.

The agents as contemplated herein lead to significantly increased strengthening of the internal and external hair structure. A further subject of the present disclosure is therefore the use of agents as contemplated herein for strengthening the hair structure, in particular the internal hair structure. Within the meaning of the present disclosure, "structure strengthening" is understood to mean a reduction in the damage to keratin fibers caused by a wide range of influences. The re-establishment of the natural strength, for example, plays a key role in this respect. Restructured fibers are distinguished for example by improved shine, by an improved feel, and by higher combability. In addition, they have optimized strength and elasticity. Successful structure strengthening or restructuring can be verified physically as an increase in the melting point by comparison with damaged fibers.

The agents as contemplated herein also lead to a considerably increased stability of artificial colors against the washout of the color. Chemically colored hair can thus be washed much more frequently using the agents as contemplated herein, without this leading to undesired bleeding or fading of the color.

A further subject of the present disclosure is therefore the use of agents as contemplated herein for reducing the washout of color from chemically colored hair.

The statements made about the agents as contemplated herein apply, mutatis mutandis, to particularly preferred embodiments of the method as contemplated herein and to the uses as contemplated herein.

EXAMPLES (ALL VALUES IN WT. %)

Hair Shampoo

|  | 1 | 2 | 3 | 4 | 5 | 6 |
|---|---|---|---|---|---|---|
| Sodium laureth sulfate | 10 | 10 | 10 | 10 | 10 | 10 |
| Cocoamidopropyl betaine | 4.0 | 4.0 | 4.0 | 4.0 | 4.0 | 4.0 |
| Ammonium lauryl sulfate | 4.0 | 4.0 | 4.0 | 4.0 | 4.0 | 4.0 |
| Polyquaternium-10 | 0.3 | 0.3 | 0.3 | 0.3 | 0.3 | 0.3 |

-continued

|  | 1 | 2 | 3 | 4 | 5 | 6 |
|---|---|---|---|---|---|---|
| Cocamide MEA | 0.8 | 0.8 | 0.8 | 0.8 | 0.8 | 0.8 |
| PEG-7 glyceryl cocoate | 1.0 | 1.0 | 1.0 | 1.0 | 1.0 | 1.0 |
| Nicotinamide | 0.3 | 0.3 | 0.3 | 0.3 | 0.3 | 0.3 |
| Citric acid | 0.8 | 0.8 | 0.8 | 0.8 | 0.8 | 0.8 |
| Glyceraldehyde | 0.10 | — | — | — | — | — |
| 2-hydroxypropanal | — | 0.12 | — | — | — | — |
| 2-hydroxyhexanal | — | — | 0.15 | — | — | — |
| 2-hydroxyoctanal | — | — | — | 0.10 | — | — |
| 2-(2-hydroxyethoxy)acetaldehyde | — | — | — | — | 0.12 | — |
| Bromomalonaldehyde | — | — | — | — | — | 0.10 |
| Panthenol | 0.5 | 0.5 | 0.5 | 0.5 | 0.5 | 0.5 |
| 2-hydroxyoctanal | 1.0 | 1.0 | 1.0 | 1.0 | 1.0 | 1.0 |
| Amodimethicone/morpholinomethyl silsesquioxane copolymer | 1.0 | 2.0 | 3.5 | 1.0 | 0.8 | 1.0 |
| Laureth-2 | 1.2 | 1.2 | 1.2 | 1.2 | 1.2 | 1.2 |
| Sodium chloride | 1.3 | 1.0 | 1.0 | 1.2 | 1.1 | 1.3 |
| Water, preservative, perfume oils | up to 100 | up to 100 | up to 100 | up to 100 | up to 100 | up to 100 |

Hair Conditioner 20

|  | 1 | 2 | 3 | 4 | 5 | 6 |
|---|---|---|---|---|---|---|
| Quaternium-87 | 0.75 | 0.75 | 0.75 | 0.75 | 0.75 | 0.75 |
| Glycol distearate | 1.0 | 1.0 | 1.0 | 1.0 | 1.0 | 1.0 |
| Cetearyl alcohol | 5.0 | 5.0 | 5.0 | 5.0 | 5.0 | 5.0 |
| Guar hydroxypropyltrimonium chloride | 0.2 | 0.2 | 0.2 | 0.2 | 0.2 | 0.2 |
| Polyquaternium-37 | 0.4 | 0.4 | 0.4 | 0.4 | 0.4 | 0.4 |
| Hydrolyzed keratin | 0.1 | 0.1 | 0.1 | 0.1 | 0.1 | 0.1 |
| Shea butter | 1.5 | 1.5 | 1.5 | 1.5 | 1.5 | 1.5 |
| Behenoyl PG-trimoniumchloride | 1.5 | 1.5 | 1.5 | 1.5 | 1.5 | 1.5 |
| Distearoylethyl hydroxyethylmonium methosulfate | 0.3 | 0.3 | 0.3 | 0.3 | 0.3 | 0.3 |
| Behentrimonium chloride | 0.4 | 0.4 | 0.4 | 0.4 | 0.4 | 0.4 |
| Lactic acid | 0.1 | 0.1 | 0.1 | 0.1 | 0.1 | 0.1 |
| Glyceraldehyde | 1.2 | — | — | — | — | — |
| 2-hydroxypropanal | — | 1.0 | — | — | — | — |
| 2-hydroxyhexanal | — | — | 2.0 | — | — | — |
| 2-hydroxyoctanal | — | — | — | 1.5 | — | — |
| 2-(2-hydroxyethoxy)acetaldehyde | — | — | — | — | 1.2 | — |
| Bromomalonaldehyde | — | — | — | — | — | 1.5 |
| Amodimethicone | 0.8 | 0.8 | 0.8 | 0.8 | 0.8 | 0.8 |
| Water, preservative, perfume oils | up to 100 | up to 100 | up to 100 | up to 100 | up to 100 | up to 100 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A hair shampoo consisting of, based on its weight,
   a) from about 0.001 to about 20 wt. % of alpha-substituted aldehyde, wherein the alpha-substituted aldehyde is glyceraldehyde or bromomalonaldehyde, 2-hydroxy propanal, 2-hydroxy hexanal, 2-hydroxyoctanal or 2-(2-hydroxyethoxy)acetaldehyde
   b) from about 0.001 to about 50 wt. % of amodimethicone/morpholinomethyl silsesquioxane copolymer,
   c) Sodium laureth sulfate
   d) Cocoamidopropyl betaine
   e) Ammonium lauryl sulfate
   f) Polyquaternium-10
   g) Cocamide MEA
   h) PEG-7 glyceryl cocoate
   i) Nicotinamide
   j) Citric acid
   k) Panthenol
   l) Laureth-2
   m) Sodium chloride
   n) Water, preservative, perfume oils.

2. The hair treatment agent according to claim 1, wherein it comprises, based on its weight, from about 0.01 to about 10 wt. %, of alpha-substituted aldehyde.

3. The hair treatment agent according to claim 1, wherein it comprises, based on its weight, from about 0.01 to about 20 wt. %, of the amodimethicone/morpholinomethyl silsesquioxane copolymer.

4. A method for treating hair, wherein the hair shampoo according to claim 1 is applied to dry or wet hair, is left there for a period of from about 10 to about 300 seconds, and is rinsed out thereafter.

5. The hair treatment agent according to claim 1, wherein it comprises, based on its weight, from about 0.15 to about 5 wt. %, of amodimethicone/morpholinomethyl silsesquioxane copolymer.

6. The hair shampoo according to claim 1, wherein the alpha-substituted aldehyde is bromomalonaldehyde.

7. The hair shampoo according to claim 6, wherein it comprises, based on its weight, from about 0.1 to about 1.5 wt. %, of bromomalonaldehyde.

8. The shampoo according to claim 1, wherein the alpha-substituted aldehyde is 2-(2-hydroxyethoxy)acetaldehyde.

9. The hair shampoo according to claim 8, wherein it comprises, based on its weight, from about 0.12 to about 1.2 wt. %, of 2-(2-hydroxyethoxy)acetaldehyde.

* * * * *